(12) United States Patent
Verhaverbeke et al.

(10) Patent No.: US 6,261,845 B1
(45) Date of Patent: Jul. 17, 2001

(54) METHODS AND SYSTEMS FOR DETERMINING CHEMICAL CONCENTRATIONS AND CONTROLLING THE PROCESSING OF SEMICONDUCTOR SUBSTRATES

(75) Inventors: Steven Verhaverbeke, Radnor; Gerald N. DiBello, West Chester; Christopher F. McConnell, Berwyn, all of PA (US)

(73) Assignee: CFMT, Inc., Wilmington, DE (US)

( * ) Notice: Subject to any disclaimer, the term of this patent is extended or adjusted under 35 U.S.C. 154(b) by 0 days.

(21) Appl. No.: 09/257,488

(22) Filed: Feb. 25, 1999

(51) Int. Cl.$^7$ ............................................. G01N 35/08
(52) U.S. Cl. ............................ 436/55; 134/18; 438/8
(58) Field of Search ..................... 436/43, 50, 51, 436/52, 55; 422/62, 81; 137/3, 5, 88, 93; 134/2, 18, 9, 26, 902, 28, 29; 438/8

(56) References Cited

U.S. PATENT DOCUMENTS

| 3,543,776 | 12/1970 | Layton ................................. 134/182 |
| 3,869,313 | 3/1975 | Jones et al. .............................. 134/73 |
| 4,560,417 | 12/1985 | Bardina et al. .......................... 134/1 |

(List continued on next page.)

FOREIGN PATENT DOCUMENTS

| 0 233 184 | 4/1992 | (EP) . |
| 56-046535 | 4/1981 | (JP) . |
| 4-065829 | 3/1992 | (JP) . |
| 9-064005 | 3/1997 | (JP) . |
| WO 87/00094 | 1/1987 | (WO) . |

OTHER PUBLICATIONS

Burkman et al., "Wet Chemical Processes–Aqueous Cleaning Processes", Handbook of Semiconductor Wafer Cleaning Technology, Kern, W. (Ed.), Noyes Publication, Parkridge, NJ, 1993, Chapter 3, 111–151.

"CFM Technologies. The Next Generation in Wet Processing" brochure, CFM Technologies, West Chester, PA.

"Full–Flow™ Wet Processing" brochure, 1993, CFM Technologies, Inc., West Chester, PA.

Gise, P. et al., "Semiconductor and Integrated Circuit Fabrication Techniques", Reston Publishing Co., Reston, VA, 1979.

(List continued on next page.)

*Primary Examiner*—Jill Warden
*Assistant Examiner*—Brian Sines
(74) *Attorney, Agent, or Firm*—Woodcock Washburn Washburn Kurtz Mackiewicz & Norris LLP

(57) ABSTRACT

The present invention provides systems and methods of determining the concentration of chemicals in a wet processing stream where the wet processing stream is formed from two or more liquid streams having known chemical concentrations. The concentration of chemicals in the wet processing stream are monitored by measuring the flow rates of the liquid streams during combination to form the wet processing stream, and calculating the concentrations of chemicals in the wet processing stream based on the flow rates and known chemical concentrations of the liquid streams. The present invention also provides systems and methods for controlling the wet processing of semiconductor substrates using the calculated concentrations in the wet processing stream. The methods and systems of the present invention are particularly useful when the semiconductor substrates are contacted with the wet processing stream in a single pass.

17 Claims, 2 Drawing Sheets

U.S. PATENT DOCUMENTS

| | | | |
|---|---|---|---|
| 4,577,650 | 3/1986 | McConnell | 134/59 |
| 4,633,893 | 1/1987 | McConnell et al. | 134/95 |
| 4,738,272 | 4/1988 | McConnell | 134/59 |
| 4,740,249 | 4/1988 | McConnell | 134/25.4 |
| 4,778,532 | 10/1988 | McConnell et al. | 134/10 |
| 4,795,497 | 1/1989 | McConnell et al. | 134/18 |
| 4,856,544 | 8/1989 | McConnell | 134/95 |
| 4,899,767 | 2/1990 | McConnell et al. | 134/56 R |
| 4,911,761 | 3/1990 | McConnell et al. | 134/11 |
| 4,917,123 | 4/1990 | McConnell et al. | 134/95 |
| 4,984,597 | 1/1991 | McConnell et al. | 134/95 |
| 5,069,235 | 12/1991 | Vetter et al. | 134/902 |
| 5,174,855 | 12/1992 | Tanaka | 156/626 |
| 5,261,966 * | 11/1993 | Mashimo et al. | 134/2 |
| 5,286,657 | 2/1994 | Bran | 437/9 |
| 5,301,701 | 4/1994 | Nafziger | 134/95.2 |
| 5,311,892 | 5/1994 | Adelt et al. | 134/58 R |
| 5,327,921 | 7/1994 | Mokuo et al. | 134/182 |
| 5,370,741 | 12/1994 | Bergman | 134/3 |
| 5,470,393 * | 11/1995 | Fukazawa | 134/3 |
| 5,472,516 | 12/1995 | Hanson et al. | 134/18 |
| 5,511,569 | 4/1996 | Mukogawa | 134/104.1 |
| 5,542,441 | 8/1996 | Mohindra et al. | 134/95.2 |
| 5,569,330 | 10/1996 | Schild et al. | 134/1 |
| 5,571,337 | 11/1996 | Mohindra et al. | 134/7 |
| 5,571,644 | 11/1996 | Uraguchi et al. | 430/30 |
| 5,578,273 | 11/1996 | Hanson et al. | 422/110 |
| 5,634,978 | 6/1997 | Mohindra et al. | 134/2 |
| 5,651,379 | 7/1997 | Mohindra et al. | 134/95.2 |
| 5,656,097 | 8/1997 | Olesen et al. | 134/1 |
| 5,685,327 | 11/1997 | Mohindra et al. | 134/95.2 |
| 5,725,753 | 3/1998 | Harada et al. | 205/746 |
| 5,733,434 | 3/1998 | Harada et al. | 205/746 |
| 5,762,684 | 6/1998 | Hayashi et al. | 95/24 |
| 5,772,784 | 6/1998 | Mohindra et al. | 134/21 |
| 5,800,626 | 9/1998 | Cohen et al. | 134/1.3 |
| 5,810,940 | 9/1998 | Fukazawa et al. | 134/3 |
| 5,858,106 | 1/1999 | Ohmi et al. | 134/1 |
| 5,934,299 * | 8/1999 | Akatsu et al. | 134/105 |
| 5,996,595 * | 12/1999 | Olesen et al. | 134/13 |

OTHER PUBLICATIONS

Horiki, H. et al., "Wet Etch Cleaning", in *Ultraclean Technology Handbook*, Ohmi, T. (ed.), Marcel Dekker, 1991, vol. 1, Ch. 3, 805–819.

Kern, W. et al., "Chemical Etching", *Thin Film Processes*, Vosser, J.L. (ed.), Academic Press, NY, 1978, vol. 1, pp. 403–447 and 452–481.

Kern, W. "Overview and Evolution of Semiconductor Wafer Contamination and Cleaning Technology", Handbook of Semiconductor Wafer Cleaning Technology, Kern, W. (Ed.), Noyes Publication, Parkridge, NJ, 1993, Chapter 1, 3–67.

Verhaverbeke, S. et al., "Scientific Rinsing and Drying on Macro and Microscale," in Semiconductor Pure Water and Chemicals Conference 1996, Balazs, M.K. (ed.), Santa Clara, CA March 4–7, 1996, 14 pages.

Verhaverbeke, S. et al., "Wet Processing Uniformity for 200mm and 300mm in one Bath Cleaning Systems", 17th Annual Semiconductor Pure Water and Chemicals Conference, Santa Clara, CA, March 2–5, 1998, 387–398.

U.S. application No. 08/684,543, Verhaverbeke et al., filed Jul. 19, 1996.

U.S. application No. 08/904,481, Myland et al., filed Jul. 31, 1997.

U.S. application No. 08/881,267, Verhaverbeke, filed Jun. 24, 1997.

U.S. application No. 09/096,898, Verhaverbeke, filed Jun. 12, 1998.

U.S. application No. 09/209,101, Verhaverbeke et al., filed Dec. 10, 1998.

* cited by examiner

METHODS AND SYSTEMS FOR DETERMINING CHEMICAL CONCENTRATIONS AND CONTROLLING THE PROCESSING OF SEMICONDUCTOR SUBSTRATES

FIELD OF INVENTION

The present invention relates to methods and systems for wet processing semiconductor substrates. More particularly, the present invention provides methods and systems for determining chemical concentrations in wet processing streams and controlling the processing of semiconductor substrates.

BACKGROUND OF INVENTION

Wet processing of semiconductor substrates, such as wafers, flat panels, and other electronic component precursors is used extensively during the manufacture of, for example, integrated circuits. Preferably, wet processing is carried out to prepare the semiconductor substrates for processing steps such as diffusion, ion implantation, epitaxial growth, chemical vapor deposition, and hemispherical silicon grain growth, or combinations thereof. During wet processing, the semiconductor substrates are contacted with a series of process solutions. The process solutions may be used, for example, to etch, to remove photoresist, to clean, or to rinse the semiconductor substrates. See, e.g., U.S. Pat. Nos. 4,577,650; 4,740,249; 4,738,272; 4,856,544; 4,633,893; 4,778,532; 4,917,123; and EPO 0 233 184, assigned to a common assignee, and Burkman et al., Wet Chemical Processes-Aqueous Cleaning Processes, pg 111–151 in Handbook of Semiconductor Wafer Cleaning Technology (edited by Werner Kern, Published by Noyes Publication Parkridge, New Jersey 1993), the disclosures of which are herein incorporated by reference in their entirety.

There are various types of systems available for wet processing. For example, the semiconductor substrates may be processed in a single vessel system closed to the environment (such as a Full-Flow™ system supplied by CFMT Technologies), a single vessel system open to the environment, or a multiple open bath system (e.g., wet bench) having a plurality of baths open to the atmosphere.

Following processing, the semiconductor substrates are typically dried. Drying of the semiconductor substrates can be done using various methods, with the goal being to ensure that there is no contamination created during the drying process. Methods of drying include evaporation, centrifugal force in a spin-rinser-dryer, steam or chemical drying of wafers, including the method and apparatus disclosed in, for example, U.S. Pat. No. 4,778,532.

A common problem encountered in the wet processing of semiconductor substrates is obtaining repeatable processing results (i.e. process control) for all surfaces of a single semiconductor substrate, between semiconductor substrates in a single batch, and between batches of semiconductor substrates that are processed in the same manner. For example, when semiconductor wafers are etched to remove oxides, it is desirable that the thickness of etching is substantially the same on all surfaces of a single wafer, as well as between wafers within the same batch. Additionally, it is desired that wafers in different batches being processed under the same etching conditions do not vary substantially in etching thickness (i.e., batch to batch variation).

Traditionally, process control in semiconductor wet processing is completed through the use of "monitor semiconductor substrates." Monitor semiconductor substrates are processed in the equipment using the same manufacturing conditions as the production semiconductor substrates. The monitor semiconductor substrates are then tested to ensure that the manufacturing process is running within its specified limits. However, the use of monitor semiconductor substrates can be costly. For example, the use of monitor semiconductor substrates leads to lost production time as well as wasted raw materials in processing the monitor semiconductor substrates.

One way to eliminate or reduce the use of monitor semiconductor substrates is to monitor processing conditions in the processing vessel and make adjustments to the processing conditions during processing. For example in an etching process for semiconductor substrates, it is known that etching thickness is a function of etching time, temperature, and chemical concentration of the etching agent. Also for example, in cleaning processes, such variables as cleaning time, temperature, use of megasonic energy, and chemical concentration can have an impact on the uniformity and efficiency of cleaning of the semiconductor substrates. Thus, processing results can be controlled through such parameters as temperature, chemical concentration, and processing time. While solution temperature and processing time can readily be controlled in most wet processing systems, the measuring and controlling of chemical concentrations has been problematic. Thus, much effort has focused on developing systems and methods for determining chemical concentrations for improved process control in wet processing systems.

For example, in U.S. Pat. No. 5,472,516 to Hanson et al., ("Hanson") a control strategy is proposed for measuring and maintaining the concentration of chemicals in a bath. In Hanson, the concentrations of ammonium hydroxide and hydrogen peroxide in an SC1 cleaning solution were monitored by measuring the pH and conductivity of the SC1 cleaning. The conductivity was used to control the addition of ammonia to the bath, and the pH was used to control the addition of hydrogen peroxide to the bath. The life of the SC1 solution was extended by the process. IR spectrometric monitors have also been used to monitor chemical concentrations in open bath systems.

In open bath systems such as the system used by Hansen, monitors may be readily placed within the bath in-situ, providing the user with real-time chemical concentration information. However, even in an open bath system, in-situ monitors, may not accurately measure chemical concentrations. For example, when there is more than one chemical present, one may not be able to accurately measure the concentration of a chemical (such as a weak acid or base) due to the presence or interaction of other chemicals (such as a strong acid or strong base) present in the bath. Often, more than one monitor may be needed to measure the concentrations of different chemicals, leading to increased costs for purchasing and maintaining the monitors. Equipment for measuring concentrations directly, such as conductivity meters, can also be unreliable. Thus there is a need for simplified ways to determine chemical concentrations in wet processing systems.

Determining chemical concentrations in a single pass wet processing vessel (where a solution is passed once through the vessel) can be further problematic. For example, in many single pass wet processing vessels, the placement of a concentration measuring device in the vessel will disrupt the flow pattern of process solution resulting in nonuniform contacting of the process solution with the semiconductor substrates. A solution would be to place the measuring devices upstream or downstream of the process vessel.

However, when the process solution contains mixtures of chemicals, more than one measuring device will most likely be needed, leading to increased costs for purchasing and maintaining several measuring devices. Additionally, it may not even be possible to accurately measure the concentration of each chemical in the process solution due interactions between the chemicals or equipment reliability problems.

Thus, there is a need for simpler methods and systems for determining chemical concentrations of wet processing streams used in a wet processing system. Further, there is a need for simpler methods and systems for controlling the processing of semiconductors in a wet processing system.

SUMMARY OF INVENTION

The present invention provides methods and systems for determining chemical concentrations of wet processing streams during wet processing. The methods and systems of the present invention are particularly useful for determining chemical concentrations in a wet processing stream where the wet processing stream is formed by combining two or more liquid streams of known chemical concentration. The systems and methods of the present invention can eliminate the need to directly measure chemical concentrations in the wet processing stream such as through conductivity meters or pH probes during wet processing.

In one embodiment of the present invention, a method for determining the concentration of chemicals is provided that includes determining initial concentrations of chemicals in one or more liquid streams; combining the one or more liquid streams to form a wet processing stream, measuring the flow rates of the liquid streams during the time the liquid streams are being combined; and calculating the concentration of the chemicals in the wet processing stream using the measured flow rates of the liquid streams and the initial concentrations of chemicals in the liquid streams.

In another embodiment, the present invention provides a method of controlling the processing of semiconductor substrates in a vessel that includes calculating the concentration of chemicals in a wet processing stream as described above; and using the calculated concentrations of the chemicals in the wet processing stream to calculate an exposure time for contacting the semiconductor substrates with the wet processing stream or a subsequent processing stream. The calculated exposure time can be used to control the exposure time of the wet processing stream or a subsequent wet processing streams with semiconductor substrates in the present batch, or in subsequent batches.

In another embodiment of the present invention, a system is provided for determining the concentration of chemicals during wet processing of semiconductor substrates that includes a vessel for holding one or more semiconductor substrates, and having an inlet and outlet for directing a wet processing stream into and out of the vessel; one or more liquid supply systems for supplying one or more liquid streams; an injection system for combining the one or more liquid streams to form a wet processing stream, where the injection system is in flow communication with the one or more liquid supply systems and the process vessel; flow rate measuring equipment for measuring the flow rates of the liquid streams during combination; and a processing system for receiving the measured flow rates from the flow rate measuring equipment and calculating the concentration of the chemicals in the wet processing streams.

In another embodiment, the present invention provides a system for controlling the wet processing of semiconductor substrates that includes the system described above where the processing system is capable of calculating an exposure time for the wet processing stream or a subsequent wet processing stream in response to the calculated chemical concentrations in the wet processing stream and is capable of controlling an actual exposure time of the wet processing stream or the subsequent wet processing stream in response to the calculated exposure time.

DETAILED DESCRIPTION OF THE INVENTION

Figure 1:
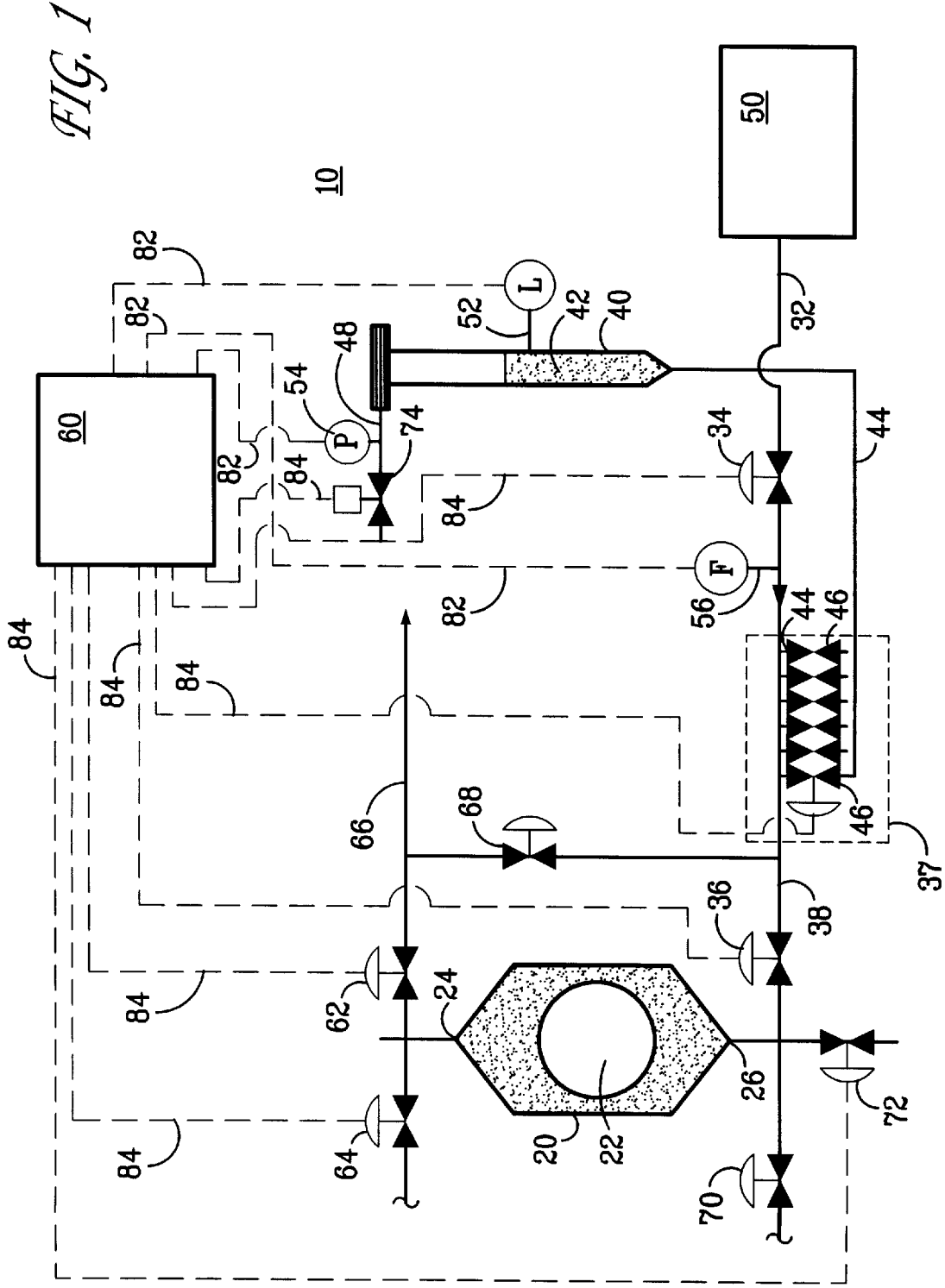
FIG. 1 shows an embodiment of a system of the present invention for controlling the wet processing of semiconductor substrates in a wet processing vessel.

The present invention provides methods and systems for determining the concentration of one or more chemicals in a wet processing stream where the wet processing stream is formed from two or more liquid streams having known chemical concentrations. The concentration of chemicals in the wet processing stream are monitored by measuring the flow rates of the liquid streams during the time the liquid streams are being combined to form the wet processing stream, and calculating the concentrations of chemicals in the wet processing stream based on the flow rates and known chemical concentrations of the liquid streams. In this manner, chemical concentrations in the wet processing stream do not need to be directly measured through such equipment as conductivity meters (although could still be) in the wet processing stream during wet processing. Also, it has been found that in-situ chemical concentration measuring equipment such as conductivity measuring equipment is often less reliable and requires more calibration in comparison to devices used for measuring liquid flow rates.

The methods and systems of the present invention for determining chemical concentrations is particularly useful for controlling the wet processing of semiconductor substrates. For example, the exposure time of the semiconductor substrates with one or more wet processing streams can be adjusted in response to the calculated concentrations. In this embodiment of the present invention it is preferred that the process vessel holding the semiconductor substrates be configured for a "single pass" so that the wet processing stream passes a single time through the vessel. A single pass configuration is preferred since multiple passes of a wet processing stream with one or more batches of semiconductor wafers, such as when recycling, can cause the concentration of chemicals in the wet processing stream to significantly change after combination of the liquid streams due to such factors as evaporation, or chemical consumption.

The methods and systems of the present invention are useful in any wet processing procedure for semiconductor substrates where a wet processing stream containing one or more chemicals is formed from the combination of two or more liquid streams. By "wet processing" it is meant that the semiconductor substrates are contacted with one or more wet processing streams to process the semiconductor substrate in a desired manner. "Wet processing" as defined herein may include for example treating, rinsing, or drying the semiconductor substrates. Typically, such wet processing is carried out to prepare the semiconductor substrate for processing steps such as diffusion, ion implantation, epitaxial growth, chemical vapor deposition, and hemispherical silicon grain growth, or combinations thereof.

By "wet processing stream" it is meant any liquid stream used during wet processing that is contacted with the semiconductor substrate and contains one or more chemicals. By "chemical" or "chemicals" it is meant any agent in a wet processing stream used to aid in processing (e.g., treat, or rinse) semiconductor substrates.

By "variation," as used herein, it is meant the difference between the target value and measured value of a variable (such as flow rate or concentration), divided by the target value of the variable.

An embodiment of a method and system of the present invention will now be described in detail with reference to FIG. 1 where like numerals refer to like elements. FIG. 1 shows an embodiment of a wet processing system 10 of the present invention for determining the concentration of chemicals in a wet processing stream and for controlling the wet processing of semiconductor substrates. Wet processing system 10 includes a process vessel 20, a first liquid stream supply system 50, an injection system (described hereinafter) and a processing system 60 that includes a processor. The process vessel 20 has a support (not shown) for holding wafers 22, and top and bottom fluid ports 24, 26 respectively. The first liquid stream supply system 50 provides a first liquid stream 32 to the process vessel 20 at a controlled rate. The injection system combines two or more liquid streams to form a wet processing stream 38. In FIG. 1, the injection system includes an injection manifold that combines one or more process solutions 42 (only one shown) held in one or more containers 40 (only one shown) with the first liquid stream 32.

In the method of the present invention, the concentrations of chemicals in the two or more liquid streams are determined (e.g., provided by the chemical supplier or analyzed) prior to combination of the liquid streams. The method and time of determining the chemical concentrations in the liquid streams are not critical as long as the concentration is known prior to combining the liquid streams to form the wet processing stream. For example, the chemical concentrations could have been determined for example by the supplier of the liquid stream, or the analysis could be performed in-situ during wet processing, immediately before use. Preferably, the concentration of chemicals in the liquid stream is determined to an accuracy of about 1 percent or lower relative to the actual chemical concentration.

The concentration of chemicals in the wet processing stream is monitored by combining two or more liquid streams to form a wet processing stream, measuring the flow rates of the liquid streams during combination, and calculating the chemical concentrations in the wet processing stream based on the measured flow rates and known chemical concentrations of the liquid streams. The liquid streams may be combined in any fashion as long as the concentration of chemicals in the wet processing stream can be determined at any time during the combination of the liquid streams. For example, all the desired chemicals in one or more liquid streams may be added at the same time to a single liquid stream. Also, for example, the addition of chemicals may be staggered so that one or more liquid streams are injected at different times into a single liquid stream. One or more liquid streams may also be added intermittently, as long as the concentration of chemicals in the wet processing stream in the process vessel can be determined. It is also possible that a non-chemical containing liquid streams be combined with other liquid streams as long as at least one chemical is present in at least one liquid stream.

Preferably, the two or more liquid streams are combined in a manner such that the flow rates of the liquid streams are accurate (e.g., preferably variations of less than about 1 percent and more preferably less than about 0.2 relative to the target value). Having accurate flow rates reduces the variability of chemical concentrations in the wet processing stream. Also, accuracy of flow rates is desirable because variability in the flow rate of one liquid stream can effect the flow rates of the other liquid streams being combined.

A preferred method and system of combining two or more liquid streams is shown in FIG. 1. In FIG. 1, an injection manifold 37 is used to combine one or more process solutions 42 with a first liquid stream 32. The injection manifold 37 is in flow communication with the first liquid stream supply system 50 and containers 40 (only one shown) that supply process solutions 42 (only one shown) via one or more process solution injection lines 44 (six shown) and one or more control valves 46 (six shown) located in each of the process solution injection lines 44. The injection of the process solutions 42 into the first liquid stream 32 is preferably accomplished by applying pressure to container 40 with a gas stream 48, such as nitrogen. The pressure directs the process solution 42 into process solution injection lines 44, through control valves 46, and into liquid stream 32. A pressure regulator 74 is preferably used to control the gas stream pressure and a pressure indicator 54 is preferably used to monitor the pressure of gas stream 48.

During combination of the liquid streams, the flow rates of the liquid streams are measured. In FIG. 1, the flow rate of first liquid stream 32 is measured using a paddle wheel flow meter 56 (such as Model M.4000 flow meter, supplied by Data Industrial located in Mattapoisett, Mass.). The flow rate of process solution 42 is measured using a capacitance level probe 52 that continuously monitors the level of process solution 42 in container 40. The flow rate of process solution 42 can then be calculated from knowing the inside cross sectional area of the container 40 and the change in level over a known time.

From the known concentrations of chemicals in the liquid streams prior to combination, and the measured flow rates of the liquid streams while being combined, the concentration of chemicals can be calculated according to techniques well known to those skilled in the art. For example, the concentration of chemicals could be calculated manually, with or without the aid of a calculator, or through the use of a processor, such as a computer, using conventional mass balance equations Preferably, a processor is used.

In FIG. 1, a processing system 60 receives instantaneous or "real-time" input 82 from the equipment for measuring flow rates (e.g., flow meter 56 and level probe 52 in FIG. 1) and calculates the concentration of chemicals in wet processing stream 38 based on this input 82 and the known concentrations of chemicals in the process solution and liquid stream.

The programming of a processor to calculate the concentration of chemicals in the wet processing stream can be performed by techniques well known to those skilled in the art. For example, conventional mass balance equations to solve for the concentration of chemicals in the wet processing stream could be programmed into the processor. Also, it may be necessary to input additional data into the processor. For example, if flow rates are given in volumetric units, it will also be necessary to input the densities of the liquid streams to convert volume flow rates to mass flow rates to calculate concentrations based on weight. Also, for example, if a chemical reaction occurs upon combination of the liquid streams, the chemical kinetics of the reaction will also need to be accounted for in calculating the chemical concentrations. Accordingly, it may be necessary to provide additional data such as reaction rates and/or equilibrium constants when chemical reactions occur. If a reaction does occur, preferably the reaction reaches completion or equilibrium quickly (i.e., prior to the wet processing stream entering the process vessel) so that changes in chemical concentration do not need to be accounted for during contacting of the semiconductor substrates with the wet processing stream.

The concentrations of each chemical are preferably calculated during combination at predetermined time intervals (e.g., every one to two seconds) based on the instantaneous or real time flow rate of the liquid streams during the time interval. The average concentration of chemicals is preferably determined by averaging the concentrations calculated at each time interval during the combination.

In FIG. 1, the wet processing stream 38, once formed from the process solutions 42 and first liquid stream 32, is directed into process vessel 20 to contact wafers 22 with wet processing stream 38 for an exposure time. The wet processing stream 38 can be directed through the vessel by various means. Preferably, the wet processing stream 38 is directed through process vessel 20 in a manner that the parts of the semiconductor substrates first exposed to the wet processing stream 38 are the first parts of the semiconductor substrates removed from the wet processing stream 38. This "first in-first out" method can be achieved for example by draining wet processing stream 38 from the process vessel 20 through a port opposite to the entrance port. Preferably, the wet processing stream 38 is directed into process vessel 20 through valve 36 to bottom port 26, and exits out of the process vessel 20 through top port 24, through valve 62, to drain line 66.

Although wet processing system 10 of FIG. 1 is shown as directing the wet processing stream 38 from the bottom port 26 to top port 24, the wet processing stream 38 could be directed in various other ways. For example, the wet processing stream 38 could be directed in top port 24 to bottom port 26 or directed both in and out of bottom port 26. Feeding from top port 24 to bottom port 26 is particularly preferred when drying the semiconductor substrates with a drying fluid. In this connection, control valve 72 may be used as a drain valve for draining the wet processing stream from the process vessel.

The removal of the wet processing stream 38 from the process vessel 20 can be performed in various ways also. For example, a rinsing fluid, drying fluid or a second wet processing stream could be directed through the process vessel 20 to displace the wet processing stream 38 currently in the vessel either through the top port 24 or bottom port 26.

Another feature shown in FIG. 1 is that to allow time for the concentration of chemicals in wet processing stream 38 to stabilize due to for example fluctuations in flow rates during start-up, the wet processing stream 38 may be directed to drain line 66 with bleed valve 68 open and control valve 36 closed. After the concentration of chemicals has stabilized, control valve 36 may be opened and bleed valve 68 closed to direct the wet processing stream into the process vessel.

In a preferred embodiment of the present invention, the calculated chemical concentrations in the wet processing stream, obtained in accordance with the methods of the present invention, are further used to control wet processing. For example, the calculated chemical concentrations can be used to calculate the exposure time of the wet processing stream or a subsequent wet processing stream with the semiconductor substrates. The subsequent wet processing stream can be for example, contacted with the same batch of semiconductor substrates or a subsequent batch of semiconductor wafers. Preferably, the calculated concentrations of a wet processing stream are used to calculate the exposure time of the same wet processing stream with the semiconductor substrates. By "exposure time," it is meant the total time a semiconductor substrate is exposed to the wet processing stream. For example, for the system shown in FIG. 1, the exposure time includes the time the semiconductor substrates are exposed to the wet processing stream while filling the vessel, the time the semiconductor substrates are soaked in the wet processing stream (e.g., a static or moving wet processing stream) and the time the semiconductor substrates are exposed to the wet processing stream during removal of the wet processing stream from the vessel.

The exposure time may be determined manually or with the aid of a processor such as a computer. Preferably, the exposure time is determined by a processor. Preferably, the processor then either directly or indirectly controls the exposure time of the semiconductor substrates with the wet processing solution. For example, in the case of direct control, the processor could directly control the opening and closing of valves to control the exposure time. In the case of indirect control, the processor may for example send the exposure time to one or more controllers that control the wet processing system.

The calculation of exposure time will depend on such variables as the concentrations of the chemicals in the wet processing stream, temperature of the wet processing stream, and desired result (e.g., etch depth or degree of cleaning). For example, in etching with an etching solution of hydrofluoric acid, it is known that the etching time will depend on the concentration of hydrofluoric acid in the etching solution, the temperature of the etching solution, and the desired etch depth. One skilled in the art will be able to provide suitable equations for manually calculating an exposure time or programming a processor to calculate contact time based on such variables. Such equations may be obtained theoretically, through experimentation, or a combination of both.

Once an exposure time is determined based on the calculated chemical concentrations in the wet processing stream, there are various ways in which the wet processing system may be controlled. The control may be performed manually or automatically through the use of one or more processors or controllers. The control may additionally be performed through the manipulation of various processing parameters. For example, if the exposure time includes filling the vessel with a wet processing stream, soaking the semiconductor substrates in the wet processing stream, and removing the wet processing stream from the vessel, the exposure time could be adjusted by increasing or decreasing the soak time before sending the next wet processing stream, rinsing solution, or drying solution into the vessel. The adjustment of the exposure time could also be performed by changing the flow rate of the wet processing stream that is directed into the vessel.

FIG. 1 shows a preferred control strategy for controlling the wet processing of semiconductor substrates. In FIG. 1, the processing system 60 sends signals 84 to control the opening and closing of control valves 34, 36, 46, 62, 64 and 72, and pressure regulator 74. For example, the exposure time could be controlled through sending of the next wet processing stream at the appropriate time by the processing system 60 sending signals to control valves 34, 36, and 62 to open (with all other control valves closed). In the case of supplying a drying fluid stream to top port 24, the processing system 60 could send signals to control valves 64 and 72 to open at the appropriate time (with all other valves closed). The processing system 60 could also be used to send signals to adjust the flow rate of the wet processing stream 38 to increase or decrease the exposure time. One skilled in the art will recognize that there are various ways to control the wet processing of the semiconductor substrates. Accordingly, the above examples of process control strategies are given as examples only and are in no way intending to be limiting.

A preferred control strategy useful in the systems and methods of the present invention has the processing system 60, in addition to receiving the flow rates for the liquid streams, receiving the temperature of the wet processing stream. If the processing system 60 detects a variation of temperature and/or concentration, the processing system 60 can calculate the effect of the variation in temperature and/or concentration on exposure time, and automatically adjust the exposure time to obtain the desired result.

For example, in the case of achieving a desired etch depth, the etch depth can be estimated, (assuming a first order reaction rate) using the following equation 1:

$$\text{Etch Depth} = A \times e^{\frac{-E_a}{kT}} \times t \times C \qquad \text{Equation 1}$$

where A is a proportionality constant, k is the Boltzmann constant, T is temperature of the wet processing stream, t is target exposure time, and C is target chemical concentration of the etching agent in the wet processing stream. From Equation 1, the partial derivative of etch depth (E) with respect to concentration and time are shown in Equations 2 and 3 respectively:

$$\frac{\partial E}{\partial C} = A \times e^{\frac{-E_a}{kT}} \times t \times \Delta C \qquad \text{Equation 2}$$

$$\frac{\partial E}{\partial t} = A \times e^{\frac{-E_a}{kT}} \times C \times \Delta t \qquad \text{Equation 3}$$

Since the partial derivative of etch depth with respect to time and concentration is desired to be zero, setting Equation 2 equal to Equation 3 results in Equation 4:

$$\frac{\Delta t}{t} = \frac{\Delta C}{C} \qquad \text{Equation 4}$$

where ΔC is the change in concentration (target concentration minus calculated concentration) and Δt is the adjustment made to the target exposure time. These equations are accurate assuming that process variations are small. For example, preferably the variation in concentration is less than 2 percent and more preferably less than 1 percent. The temperature preferably is maintained within 1° C. of the target temperature and more preferably within 0.5° C.

In another preferred process control strategy, the processing system 60 in FIG. 1, in addition to adjusting the exposure time for variations in chemical concentrations, will also adjust the flow rate of the process solution 42 if the processing system 60 detects a variation of process solution 42 flow rate of greater than about 10%. This adjustment in flow rate can be made for example by using pressure regulator 74 to adjust the pressure of gas delivered to container 40.

When the calculated chemical concentrations are used for controlling wet processing, the methods and systems of the present invention are most effective when the wet processing solution is only contacted with one batch of semiconductor substrates in a single pass through the process vessel. In this manner, there is little deviation in the calculated chemical concentrations in comparison to the actual chemical concentrations that the semiconductor substrates are exposed to in the process vessel. For example, there will not be significant variations in concentration due to evaporation or chemical consumption prior to semiconductor substrate exposure.

The liquid streams that are combined to form the wet processing stream may be of any type used in wet processing as long as at least one of the liquid streams contains one or more chemicals.

The chemicals contained in at least one of the liquid streams may be any chemical that is used in the wet processing of semiconductor substrates. Examples of chemicals include those chemicals used for removing organic or inorganic materials in such wet processing steps as cleaning, etching, or removing photoresists (i.e., treating steps). Chemicals may also be used to enhance rinsing or drying. Suitable chemicals that may be used include for example hydrochloric acid, hydrogen peroxide, sulfuric acid, ozone, hydrofluoric acid, chromic acid, phosphoric acid, acetic acid, nitric acid, ammonium fluoride buffered hydrofluoric acid, ammonium fluoride, surfactants, or combinations thereof.

In a preferred embodiment of the present invention, one liquid stream is a carrier stream that dilutes chemicals contained in one or more process solutions. An example of this preferred embodiment is shown in FIG. 1, where the first liquid stream 32 is a carrier stream and one or more process solutions are fed to the first liquid stream 32 through the injection manifold 37.

Process solutions that are supplied to the carrier stream are preferably in a concentrated form that are readily available from chemical suppliers. Examples of readily available process solutions include for example 31 wt % aqueous hydrogen peroxide, 28 wt % aqueous $NH_4OH$, 37 wt % aqueous hydrochloric acid, 49 wt % aqueous hydrofluoric acid, or 98 wt % sulfuric acid.

The carrier stream is preferably a solvent that is compatible with the chemicals being used and delivers the chemicals to the surfaces of the semiconductor substrates for treatment. The carrier stream may also be used during wet processing as a rinsing solution. A preferred carrier stream is deionized water. Other carrier streams include for example organic solvents, mixtures of organic solvents, mixtures of organic solvents and water, ozonated water or combinations thereof. Suitable organic solvents include alcohols such as methanol, ethanol, 1-propanol, isopropanol, n-butanol, secbutanol, tertbutanol, or tert-amyl alcohol, acetone, acetonitrile, hexafluoroacetone, nitromethane, acetic acid, propionic acid, ethylene glycol mono-methyl ether, difluoroethane, ethyl acetate, isopropyl acetate, 1,1,2-trichloro-1,2,2-trifluoroethane, 1,2-dichloroethane, trichloroethane, perfluoro-2-butyltetrahydrofuran, perfluoro-1,4-dimethylcyclohexane or combinations thereof. Preferable organic solvents are $C_1$ to $C_6$ alcohols, such as for example methanol, ethanol, 1-propanol, isopropanol, n-butanol, secbutanol, tertbutanol, tert-amyl alcohol, pentanol, hexanol or combinations thereof.

The wet processing streams formed from the liquid streams may be used for example to treat or rinse the semiconductor substrates in the process vessel. Examples of wet processing streams used to treat semiconductor substrates include cleaning solutions, etching solutions, or solutions to remove photoresists. These solutions contain one or more chemicals to achieve the desired treatment.

For example, cleaning solutions typically contain chemicals effective in removing particles, or organics such as waxes, residual polish, or grease. Chemicals used for cleaning are typically corrosive agents, such as acids or bases. Suitable acids for cleaning include for example sulfuric acid, hydrochloric acid, nitric acid, or aqua regia. Suitable bases include for example, ammonium hydroxide. The desired concentration of the corrosive agent in the cleaning solution will depend upon the particular corrosive agent chosen and the desired amount of cleaning. These corrosive agents may also be used with oxidizing agents such as ozone or hydrogen peroxide.

Preferred cleaning solutions are "SC1" solutions containing water, ammonia, and hydrogen peroxide, and "SC2" solutions containing water, hydrogen peroxide, and hydrochloric acid. Typical concentrations for SC1 solutions range from about 5:1:1 to about 200:1:1 as parts by volume Water: $H_2O_2:NH_4OH$. Typical concentrations for SC2 solutions range from about 5:1:1 to about 1000:0:1 by volume Water: $H_2O_2:HCl$.

Suitable etching solutions contain agents that are capable of removing oxides. A common etching agent used is for example hydrofluoric acid, hydrofluoric acid buffered with ammonium fluoride, ammonium fluoride, or other substances which generate hydrofluoric acid in solution. A hydrofluoric acid containing etching solution may contain for example from about 4:1 to about 1000:1 parts by volume Water: HF. Solutions used to remove photoresists include for example solutions containing sulfuric acid, and an oxidizing substance such as hydrogen peroxide, ozone or combinations thereof.

In addition to wet processing streams used for treating semiconductor substrates, wet processing streams can be used for rinsing. In this case however, the wet processing streams preferably contain low levels of chemicals (e.g., about 1000 ppm or less). The rinsing wet processing streams may include for example hydrochloric acid, hydrofluoric acid, hydrogen peroxide, ozone, surfactants, or combinations thereof.

One skilled in the art will recognize that there are various wet processing streams that can be used during wet processing. Additional wet processing streams are disclosed in "Chemical Etching" by Werner Kern et al., in *Thin Film Processes,* edited by John L. Vosser et al., published by Academic Press, NY 1978, pages 401–496, which is incorporated by reference in its entirety.

The particular wet processing streams used, the sequence of the wet processing streams, the exposure time, and processing conditions (i.e., temperature, concentration, and flow rates) will vary depending on the particular purpose of the particular wet process. Additionally, other fluids (e.g., liquid, vapor, gas, or combinations thereof) may be contacted with the semiconductor substrates during wet processing.

Preferably, wet processing in accordance with the methods of the present invention will include contacting the semiconductor substrates with at least one wet processing stream. Wet processing may also include contacting the semiconductor substrates with rinsing fluids. "Rinsing fluids" are fluids used to wet the semiconductor substrates in preparation for subsequent wet processing steps, remove previous wet processing streams, and/or remove other contaminants such as particles from the semiconductor substrates. In selecting a rinsing fluid, such factors as the nature of the surfaces of the semiconductor substrates to be rinsed, the nature of contaminants present on the semiconductor substrates, and the nature of wet processing stream to be rinsed may be considered. Suitable rinsing fluids include those fluids previously described as being suitable for carrier streams.

An example of a suitable wet processing sequence includes contacting the semiconductor substrates with an SC1 solution (such as a 80:3:1 parts by volume of water: hydrogen peroxide: ammonium hydroxide), or an SC2 solution (such as parts by volume 80:1:1 water: hydrogen peroxide: hydrochloric acid), rinsing with deionized water, contacting the semiconductor substrates with an etching solution (such as hydrofluoric acid solution), and rinsing with deionized water. Another example of wet processing could include contacting the semiconductor substrates with a sulfuric acid/hydrogen peroxide solution and rinsing with deionized water. Preferably, the last wet processing step prior to drying is a rinse step. Thus there are various ways in which the semiconductor substrates could be wet processed in accordance with the method of the present invention. One skilled in the art would recognize that the methods of the present invention may be applied to other types of wet processing steps where chemical concentrations need to be monitored.

Following wet processing with at least one wet processing solution, the semiconductor substrates are preferably dried. By "dry" or "drying" it is meant that the semiconductor substrates are preferably made substantially free of liquid droplets. By removing liquid droplets during drying, impurities present in the liquid droplets do not remain on the surfaces of the semiconductor substrates when the liquid droplets evaporate. Such impurities undesirably leave marks (e.g., watermarks) or other residues on the surfaces of the semiconductor substrates. However, it is also contemplated that drying may simply involve removing a wet processing stream or rinsing fluid, for example with the aid of a drying fluid.

Any method and system of drying may be used. Suitable methods of drying include for example evaporation, centrifugal force in a spin-rinser-dryer, steam or chemical drying, or combinations thereof.

A preferred method of drying uses a drying fluid to directly displace the last fluid that the semiconductor substrates are contacted with prior to drying (hereinafter referred to as "direct displace drying"). Suitable methods and systems for direct displace drying are disclosed in for example U.S. Pat. Nos. 4,778,532, 4,795,497, 4,911,761, 4,984,597, and 5,569,330. Other direct displace dryers that can be used include Marangoni type dryers supplied by manufacturers such as Steag, Dainippon, and YieldUp. Most preferably, the system and method of U.S. Pat. No. 4,7911, 761 is used for drying the semiconductor substrates.

Preferably, the drying fluid is formed from a partially or completely vaporized drying solution. The drying fluid may be for example superheated, a mixture of vapor and liquid, or saturated vapor. Examples of drying solutions which may be employed are steam, alcohols such as methanol, ethanol, 1-propanol, isopropanol, n-butanol, secbutanol, tertbutanol, or tert-amyl alcohol, acetone, acetonitrile, hexafluoroacetone, nitromethane, acetic acid, propionic acid, ethylene glycol mono-methyl ether, difluoroethane, ethyl acetate, isopropyl acetate, 1,1,2-trichloro-1,2,2-trifluoroethane, 1,2-dichloroethane, trichloroethane, perfluoro-2-butyltetrahydrofuran, perfluoro-1,4-dimethylcyclohexane or combinations thereof. Preferably, the drying solution is a $C_1$ to $C_6$ alcohol, such as for example methanol, ethanol, 1-propanol, isopropanol, n-butanol, secbutanol, tertbutanol, tert-amyl alcohol, pentanol, hexanol or combinations thereof.

As previously described, the wet processing system of the present invention includes a process vessel, a liquid stream supply system, an injection system, flow rate measuring equipment, and a processing system 60. This wet processing system is preferably operated in accordance with the methods described herein.

The process vessel useful in the present invention is any vessel capable of contacting one or more semiconductor substrates located in the vessel (i.e., a batch) with a wet processing stream. Suitable process vessels include for example single vessel systems, multiple vessel systems, and spray cleaning systems. See, e.g., Chapter 1: Overview and Evolution of Semiconductor Wafer Contamination and Cleaning Technology by Werner Kern and Chapter 3: Aqueous Cleaning Processes by Don C. Burkman, Donald Deal, Donald C. Grant, and Charlie A. Peterson in Handbook of Semiconductor Wafer Cleaning Technology (edited by Werner Kern, Published by Noyes Publication Parkridge, New Jersey 1993), Wet Etch Cleaning by Hiroyuki Horiki and Takao Nakazawa in Ultraclean Technology Handbook, Volume 1, (edited by Tadahiro Ohmi published by Marcel Dekker), and U.S. Pat. No. 5,656,097 to Olesen et. al., the disclosures of which are herein incorporated by reference in their entirety.

In a preferred embodiment of the invention, the semiconductor substrates are housed in a single process vessel. Additionally, the single process vessel is preferably operated in a manner that the wet processing stream only passes one time through the process vessel (i.e., a single pass process vessel). In this manner, the concentration of chemicals in the wet processing stream can be more accurately predicted from the measured flow rates of the liquid streams being combined to form the wet processing solution. Preferable, single vessel systems used include those disclosed in U.S. Pat. Nos. 4,778,532, 4,917,123, 4,911,761; 4,795,497, 4,899,767, 4,984,597 4,633,893; 4,917,123; 4,738,272; and 4,577,650, the disclosures of which are herein incorporated by reference in their entirety. Preferred commercially available single vessel systems are Full-Flow™ vessels such as those manufactured by CFM Technologies. Such systems are preferred because the design readily allows for a sequence of wet processing streams to be passed once through the vessel to process a batch of semiconductor substrates.

The liquid stream supply system is any type of equipment that can provide one or more liquid streams to the injection system at a controlled flow rate. Preferably, the liquid stream supply system is capable of providing liquid streams to a wet processing system with a variation in flow rate of less than 1 percent and more preferably with a variation of less than 0.5 percent in flow rate.

The liquid stream supply system may include for example a tank or container equipped with pressurized gas for holding and directing one or more liquid streams from the tank or container to the injection system. The liquid stream supply system may also include one or more control valves for metering the flow of the liquid stream. The liquid stream supply system instead of, or in addition to having pressurized gas, could have a pump to deliver the liquid stream to the vessel. The liquid stream supply system may also optionally be equipped with degassification equipment to degasify the liquid stream prior to introduction into the process vessel. When the liquid stream is deionized water, the liquid stream supply system may also have equipment for deionizing water such as ion exchange columns.

Because wet processes often use multiple chemicals in one wet processing stream (e.g., SC1 or SC2 solution), the system of the present invention preferably includes multiple liquid stream supply systems. For example, the wet processing system may have a liquid supply system for deionized water, hydrogen peroxide, ammonium hydroxide, hydrochloric acid, hydrofluoric acid. In FIG. 1, the first liquid stream supply system 50 could be used for example to supply deionized water to the injection manifold 37. Other liquid streams such as ammonium hydroxide solution or hydrogen peroxide solution could be separately stored in containers 40 and delivered to the injection manifold separately via process solution chemical injection lines 44.

The injection system useful in the present invention is any type of system capable of combining two or more liquid streams to form a wet processing stream. Preferably the injection system is capable of uniformly mixing the liquid streams together.

In a preferred embodiment, the injection system includes an injection manifold 37 for combining one or more process solutions 42 with a first liquid stream 32 via one or more injection lines 44 as shown in FIG. 1. As shown in FIG. 1, the injection system is in flow communication with the liquid supply systems (i.e., the first liquid supply system 50 and the one or more containers 40 that hold the process solutions). One skilled in the art would recognize that there are various injection systems that would be capable of combining two or more liquid stream to form a wet processing stream.

Flow rate measuring equipment useful in the present invention may be any type of equipment useful for measuring the instantaneous (or real-time) flow rate of the liquid streams. By "instantaneous" it is meant that there is preferably substantially no delay between the flow measurement and the availability of the measurement for further use. Other suitable equipment (in addition to level probes and paddle wheel flow meters) for measuring flow rates of the liquid streams include for example an ultrasonic flow meter, a vortex flow meter, or a rotometer. The flow rates obtained from the flow rate measuring equipment may be for example mass flow rates or volumetric flow rates, or any other type of flow rate from which the concentration of chemicals in the wet processing stream can be calculated knowing the concentration of chemicals in the liquid streams. Preferably the flow rate measuring equipment chosen has a percent error of 1 percent or less and more preferably 0.2 percent or less. The most preferred equipment for measuring flow rates are level probes for the process solutions and paddle wheel flowmeters for the carrier stream.

The processing system used in the present invention is preferably any type of system capable of receiving data necessary for calculating the chemical concentrations in the wet processing stream and performing the chemical concentration calculations. For example, the processing system may receive liquid stream flow rates, liquid stream and wet processing stream temperatures, and liquid stream chemical concentrations to calculate the concentration of chemicals in the wet processing stream. Preferably, the processing system also calculates a desired exposure time based on the calculated concentrations.

The processing system is also preferably capable of outputting the chemical concentration calculations for further use. For example, the processing system could provide the calculations to a user, to a processor for further processing of the information, or to a controller for automatically controlling the wet processing system.

In a preferred embodiment of the present invention the calculations (concentrations or exposure times) are received by a controller that sends signals to the wet processing system to adjust the wet processing variables such as exposure time. The controller may be for example part of the processing system used to perform the calculations or a separate control system. In FIG. 1, the controller is part of processing system 60 and is therefore not shown.

Processing systems suitable for use in the present invention include for example processors such as personal computers, programmable logic controllers (PLCs), or embedded processors. Preferred processors include PLCs, such as those manufactured by Alan Bradley. The processing system may also include one or more controllers. Suitable controllers for use in the present invention include for example the processors previously described.

The methods and systems of the present invention described are advantageous in that repeated chemical concentration measurements of the same wet processing stream is not required. Instead, a single chemical concentration calculation is performed based on flow rate measurements that provide accurate chemical concentration information that can be used to control the wet processing. Additionally, the methods and systems of the present invention are particularly advantageous when measuring concentrations of chemicals in liquids having a strong acid or base in combination with a weak acid or base (i.e., the strong acid or base "masks" the presence of the weak acid or base). Examples of such liquids include SC1 and SC2 solutions previously described.

EXAMPLE

The following Example demonstrates the effectiveness of the present invention to monitor the concentration of chemicals in accordance with the methods and systems of the present invention.

Example

A CFM Full-Flow™ system Model No. 8100 was fully loaded with 8" diameter wafers. The equipment set-up was similar to that shown in FIG. 1 to etch the wafers with a hydrofluoric acid solution. The system used included separate liquid supply systems for deionized water and concentrated 49 wt % hydrofluoric acid. The system also had an Alan Bradley PLC processor for receiving flow rate data for the liquid streams.

The wafers were first contacted with deionized water at a flow rate of 18 gpm and temperature of 40° C. for 5 minutes to wet the wafers. After wetting the wafers, a hydrofluoric acid wet processing stream was formed by injecting at a predetermined flow rate 49 wt % concentrated hydrofluoric acid solution into a deionized water stream flowing at a rate of 18 gpm per min. The concentrated hydrofluoric acid was held in a container having a cross sectional area of 18 cm$^2$ and was injected into the stream of deionized water through the use of nitrogen pressure. The flow rate of deionized water was monitored with a paddle wheel flow meter. The flow rate of the concentrated hydrofluoric acid solution was monitored using a Drexel-brook level probe, located in Horsham, Pa. The flow rate of the concentrated hydrofluoric acid solution was calculated based on the cross sectional area of the container and change in level of the container over time.

After forming the hydrofluoric acid wet processing stream, the wet processing stream was injected into the vessel at a flow rate of 18 gpm to displace the deionized water and to fill the vessel with the wet processing stream. After filling the vessel, the wafers were soaked with the hydrofluoric acid wet processing stream for 5 minutes.

Following soaking, the hydrofluoric acid wet processing stream was displaced with deionized water delivered into the vessel at alternating flow rate cycles of 12 and 24 gpm for a total rinsing time of 10 min, each flow rate cycle being about 30 seconds in time.

Following rinsing, the wafers were dried with a drying vapor of isopropanol directed into the vessel at a pressure of 1.5 psig for 9 minutes.

During wet processing the concentration of the hydrofluoric acid in the hydrofluoric acid wet processing stream was directly measured using an Electro-Chemical Devices conductivity meter (located in Yarba Linola, Calif.), and also was calculated in accordance with the methods of the present invention using the average flow rates of deionized water and concentrated hydrofluoric acid solution during combination. For example, if the average flow rate of deionized water was 18 gpm and the average flow rate of concentrated hydrofluoric acid solution was 0.18 gpm during combination, the calculated concentration of hydrofluoric acid in the wet processing stream was 100:1 by volume or 0.286 mol/l.

Figure 2:
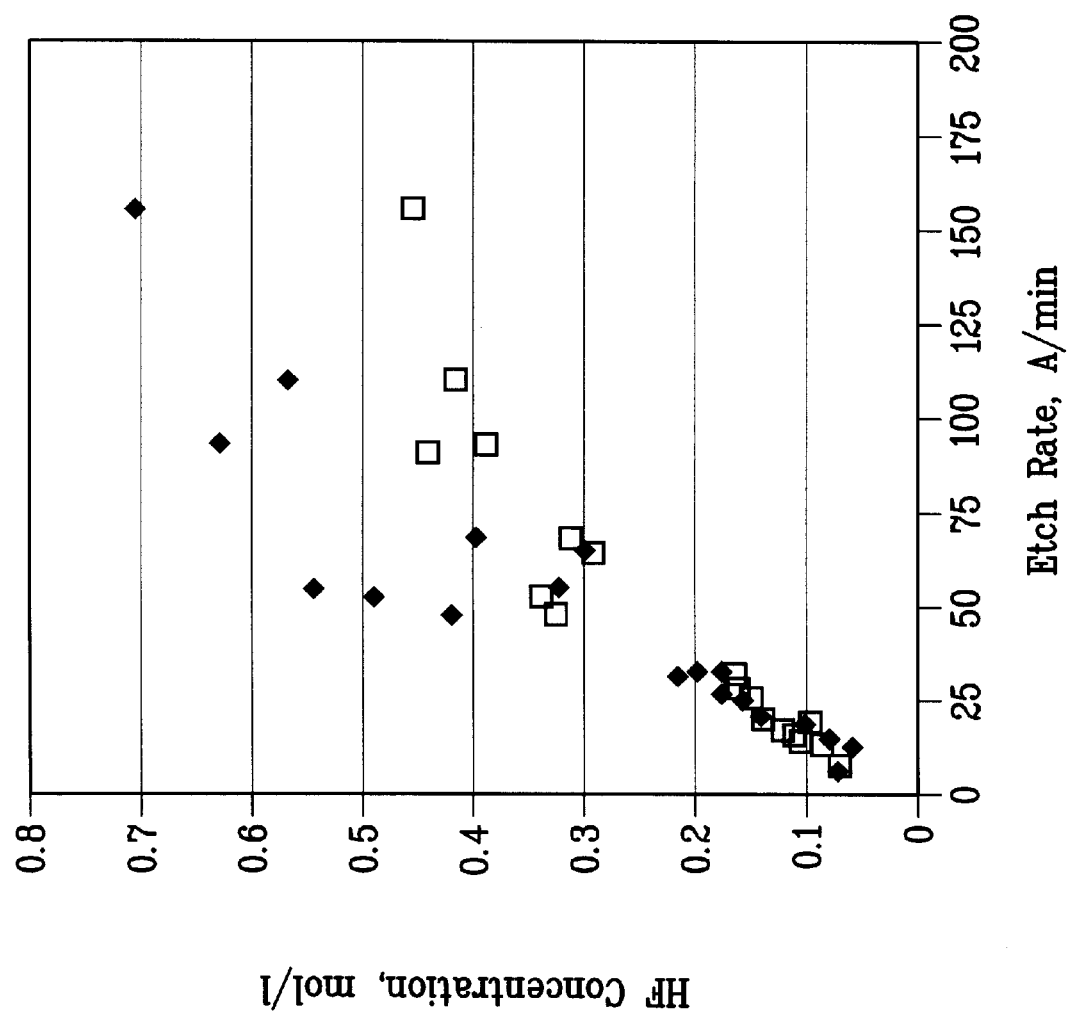
FIG. 2 shows the measured etch rate in Angstroms per minute (Å/min) of wafers exposed to a hydrofluoric acid solution versus the concentration of hydrofluoric acid in the hydrofluoric acid solution (HF Conc., in moles per liter) as determined by (A) conductivity measurements (solid marks) and (B) calculations based on flow rate measurements (open square marks).

Selected wafers from the vessel were then analyzed for etching rate using a Rudolph Caliber 300 Elipsometer located in Flanders, N.J. The measured etching rate was plotted against (A) the hydrofluoric acid concentration measured by a conductivity probe located in he drain line and (B) the hydrofluoric acid concentration calculated using the measured flow rates of concentrated hydrofluoric acid and deionized water. The plot is shown in FIG. 2 and the data actually used to form the plot is shown in Table 1.

TABLE 1

Measured Etch Rate versus Measured and Calculated HF Concentrations

| Etch Rate | Hydrofluoric Acid Concentration (mol/l) | |
|---|---|---|
| (Å/min) | Measured | Calculated |
| 7 | 0.069 | 0.072 |
| 13 | 0.061 | 0.087 |
| 18 | 0.101 | 0.098 |
| 14 | 0.081 | 0.107 |
| 16 | 0.118 | 0.115 |
| 17 | 0.121 | 0.124 |
| 20 | 0.138 | 0.141 |
| 26 | 0.161 | 0.152 |
| 27 | 0.175 | 0.158 |
| 32 | 0.201 | 0.164 |
| 32 | 0.217 | 0.175 |
| 64 | 0.298 | 0.292 |
| 68 | 0.396 | 0.311 |
| 55 | 0.545 | 0.321 |
| 48 | 0.419 | 0.328 |
| 53 | 0.489 | 0.336 |
| 93 | 0.628 | 0.385 |
| 109 | 0.567 | 0.413 |
| 91 | 0.438 | 0.438 |
| 156 | 0.705 | 0.452 |

FIG. 2 shows the hydrofluoric acid concentration (HF Conc.) in moles per liter (mol/l) versus the measured etch rate in Angstroms per minute (A/min). The open-shaped square marks represent the calculated hydrofluoric acid concentrations based on measured flow rates and the solid marks on the plot represent the measured hydrofluoric acid concentrations using the conductivity probe.

As can be seen by FIG. 2, the calculated HF concentrations have less variation, and conform to what one skilled in the art would expect for a graph showing etch rate versus concentration of HF.

Although the present invention has been described above with respect to particular preferred embodiments, it will be apparent to those skilled in the art that numerous modifications and variations can be made to those designs. The descriptions provided are for illustrative purposes and are not intended to limit the invention.

What is claimed is:

1. A method of determining the concentration of chemicals in a wet processing stream that is contacted with a batch of one or more semiconductor substrates comprising:

(a) determining initial concentrations of chemicals in one or more liquid streams;

(b) combining the one or more liquid streams to form a wet processing stream and measuring the flow rates of the liquid streams during the combination; and (c) calculating the concentration of the chemicals in the wet processing stream using the measured flow rates of the liquid streams and the initial concentrations of chemicals in the liquid streams; and (d) using the calculated concentrations of the chemicals in the wet processing stream to calculate an exposure time for contacting the semiconductor substrates with the wet processing stream or a subsequent wet processing stream, (e) contacting the batch of semiconductor substrates with the wet processing stream for the calculated exposure time.

2. The method of claim 1 wherein the one or more liquid streams comprise a carrier stream and one or more process solutions and wherein the liquid streams are combined by feeding the process solutions into the carrier stream.

3. The method of claim 2 wherein the process solutions are held in containers and the flow rates of the process solutions are measured using level indicators located in the containers.

4. The method of claim 1 wherein the calculation is performed by a processor.

5. The method of claim 1 wherein the wet processing stream is contacted only once with the batch of semiconductor substrates during the process cycle.

6. A method of controlling wet processing of one or more batches of semiconductor substrates comprising:

(a) placing a batch of one or more semiconductor substrates in a vessel;

(b) determining initial concentrations of chemicals in one or more liquid streams;

(c) combining the one or more liquid streams to form a wet processing stream and measuring the flow rates of the liquid streams during the combination;

(d) calculating the concentration of the chemicals in the wet processing stream using the measured flow rates of the liquid streams and the initial concentrations of chemicals in the liquid streams; and (e) using the calculated concentrations of the chemicals in the wet processing stream to calculate an exposure time for contacting the semiconductor substrates with the wet processing stream or a subsequent wet processing stream, and wherein the wet processing stream is passed only one time through the vessel (f) contacting the semiconductor substrates with the wet processing stream for the calculated exposure time.

7. The method of claim 6 wherein the calculation of chemical concentrations in the wet processing stream and the calculation of exposure time is performed by a processor.

8. The method of claim 6 wherein the one or more liquid streams comprise a carrier stream and one or more process solutions and wherein the liquid streams are combined by feeding the process solutions into the carrier stream.

9. A system for determining the concentration of chemicals during wet processing of semiconductor substrates comprising:

(a) a vessel for holding one or more semiconductor substrates, and having an inlet and outlet for directing a wet processing stream into and out of the vessel;

(b) one or more liquid supply systems for supplying one or more liquid streams;

(c) an injection system for combining the one or more liquid streams to form a wet processing stream wherein the injection system is in flow communication with the one or more liquid supply systems and the vessel;

(d) flow rate measuring equipment for measuring the flow rates of the liquid streams during combination; and (e) a processing system for receiving the measured flow rates from the flow rate measuring equipment, calculating the concentration of the chemicals in the wet processing streams, calculating an exposure for the wet processing stream or a subsequent wet processing stream in response to the calculated concentration of the chemicals in the wet processing stream, and wherein the processing system further comprises a controller that receives the calculated exposure time and adjusts an actual exposure time of the wet processing stream or the subsequent wet processing stream in response thereto.

10. The system of claim 9 wherein the one or more liquid supply systems comprises a system for supplying a carrier stream and one or more systems for supplying process solutions.

11. A system for controlling the wet processing of semiconductor substrates comprising:

(a) a vessel for holding one or more semiconductor substrates, and having an inlet and outlet for directing a wet processing stream into and out of the vessel;

(b) one or more liquid supply systems for supplying one or more liquid streams;

(c) an injection system for combining the one or more liquid streams to form a wet processing stream, wherein the injection system is in flow communication with the one or more liquid supply systems and the vessel;

(d) flow rate measuring equipment for measuring the flow rates of the liquid streams during combination; and (e) a processing system for receiving the measured flow rates from the flow rate measuring equipment, calculating the concentration of the chemicals in the wet processing streams, calculating an exposure time for the wet processing stream or a subsequent wet processing stream in response to the calculated chemical concentrations in the wet processing stream, and controlling an actual exposure time of the wet processing stream or the subsequent wet processing stream in response to the calculated exposure time.

12. The system of claim 11 wherein the processor system comprises a processor and a controller.

13. The system of claim 11 wherein the one or more liquid supply systems comprises a system for supplying a carrier stream and one or more systems for supplying process solutions.

14. The system of claim 9 wherein the flow rate measuring equipment has a percentage of error of about 1 percent or less.

15. The system of claim 9 wherein the flow rate measuring equipment has a percentage of error of about 0.2 percent or less.

16. The system of claim 11 wherein the flow rate measuring equipment has a percentage of error of about 1 percent or less.

17. The system of claim 11 wherein the flow rate measuring equipment has a percentage of error of about 0.2 percent or less.

* * * * *